United States Patent
Gross

(10) Patent No.: US 10,164,950 B2
(45) Date of Patent: Dec. 25, 2018

(54) CONTROLLING ACCESS TO CLINICAL DATA ANALYZED BY REMOTE COMPUTING RESOURCES

(71) Applicant: KONINKLIJKE PHILIPS N.V., Eindhoven (NL)

(72) Inventor: Brian David Gross, North Andover, MA (US)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 15/367,588

(22) Filed: Dec. 2, 2016

(65) Prior Publication Data

US 2017/0085535 A1    Mar. 23, 2017

Related U.S. Application Data

(63) Continuation of application No. 14/427,324, filed as application No. PCT/IB2013/058520 on Sep. 13, 2013, now Pat. No. 9,544,151.

(Continued)

(51) Int. Cl.
*H04L 29/06* (2006.01)
*G06F 21/62* (2013.01)
(Continued)

(52) U.S. Cl.
CPC ...... *H04L 63/0428* (2013.01); *G06F 21/6245* (2013.01); *G06Q 50/22* (2013.01);
(Continued)

(58) Field of Classification Search
None
See application file for complete search history.

(56) References Cited

U.S. PATENT DOCUMENTS

2002/0150241 A1* 10/2002 Scheidt ............... H04L 9/321
                                                    380/44
2005/0027989 A1*  2/2005 Sandhu ............. H04L 63/045
                                                    713/182

(Continued)

FOREIGN PATENT DOCUMENTS

GB          2400699 A       10/2004
WO      2012023929 A1        2/2012

OTHER PUBLICATIONS

Shamir, A: "How to share a secret", communications of the ACM, Association for computing machine, Inc., vol. 22, No. 11, Nov. 1, 1979, pp. 612-613.

*Primary Examiner* — David Le

(57) ABSTRACT

A method for controlling access to data being processed by a remote computing resource includes issuing a public encryption key for a data creator from a public certificate authority, detecting an encounter with a data owner, creating private encryption keys for the data creator and the data owner in response to detecting the encounter, encrypting data being sent to the remote computing resource with the public encryption key, the data creator's private encryption key, and the data owner's private encryption key, decrypting the data based on public verification of the public encryption key and local verification of the data creator's private encryption key and the data owner's private encryption key at the remote computing resource, and controlling the data creator's access to the data by altering the permission of at least one of the public encryption key and data creator's private encryption key.

17 Claims, 4 Drawing Sheets

Related U.S. Application Data

(60) Provisional application No. 61/702,437, filed on Sep. 18, 2012.

(51) Int. Cl.
*H04L 9/08* (2006.01)
*H04L 9/32* (2006.01)
*G06Q 50/22* (2018.01)
*H04L 9/14* (2006.01)

(52) U.S. Cl.
CPC ............... *H04L 9/083* (2013.01); *H04L 9/14* (2013.01); *H04L 9/321* (2013.01); *H04L 9/3263* (2013.01); *G06F 2221/2147* (2013.01); *H04L 2209/24* (2013.01); *H04L 2209/64* (2013.01); *H04L 2209/88* (2013.01)

(56) References Cited

U.S. PATENT DOCUMENTS

| | | | |
|---|---|---|---|
| 2007/0180259 A1 | 8/2007 | Bulot et al. | |
| 2009/0002333 A1* | 1/2009 | Maxwell | G06F 3/04883 345/173 |
| 2010/0241852 A1* | 9/2010 | Sela | G06F 21/73 713/156 |
| 2013/0117554 A1* | 5/2013 | Ylonen | H04L 9/08 713/151 |

* cited by examiner

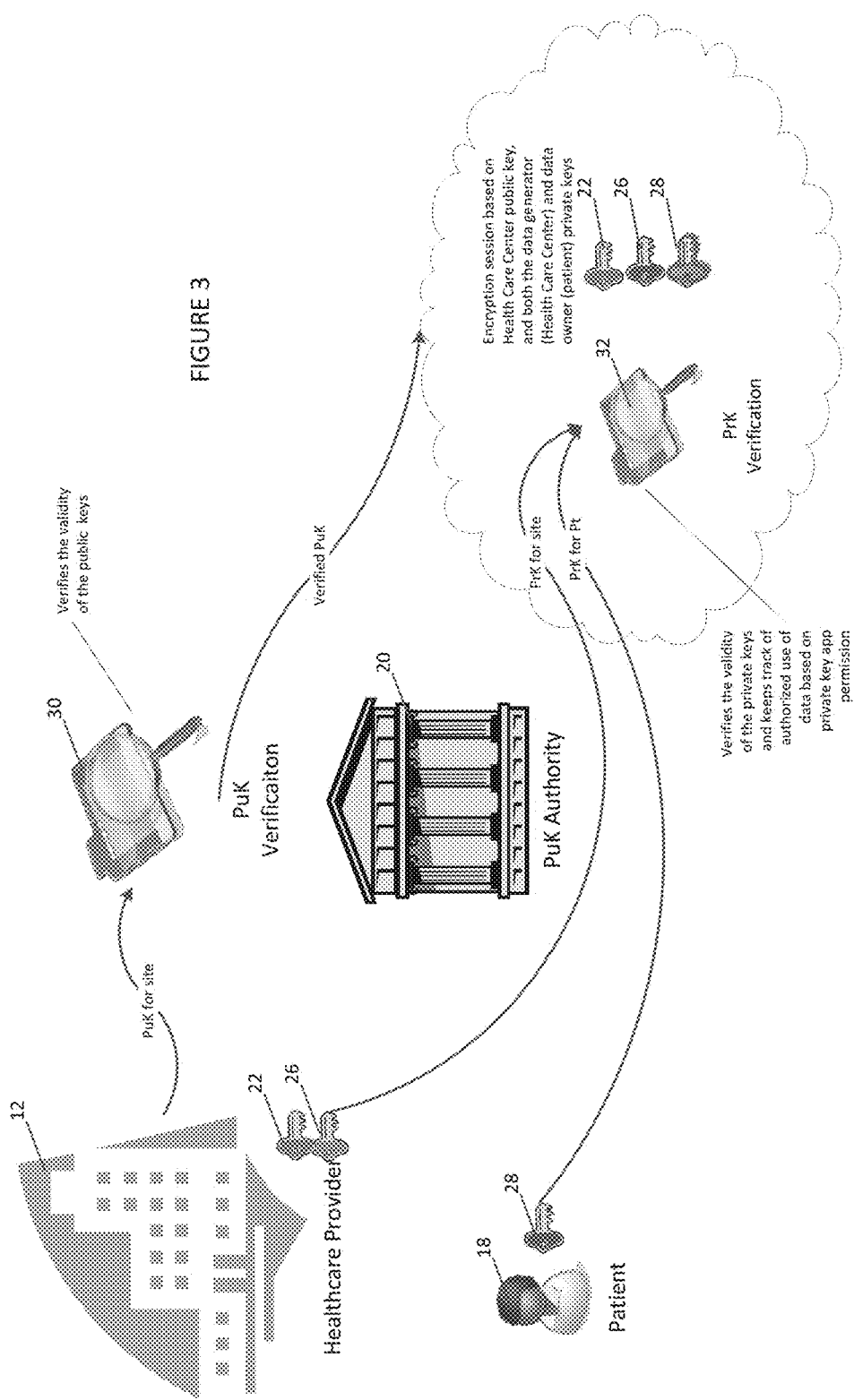

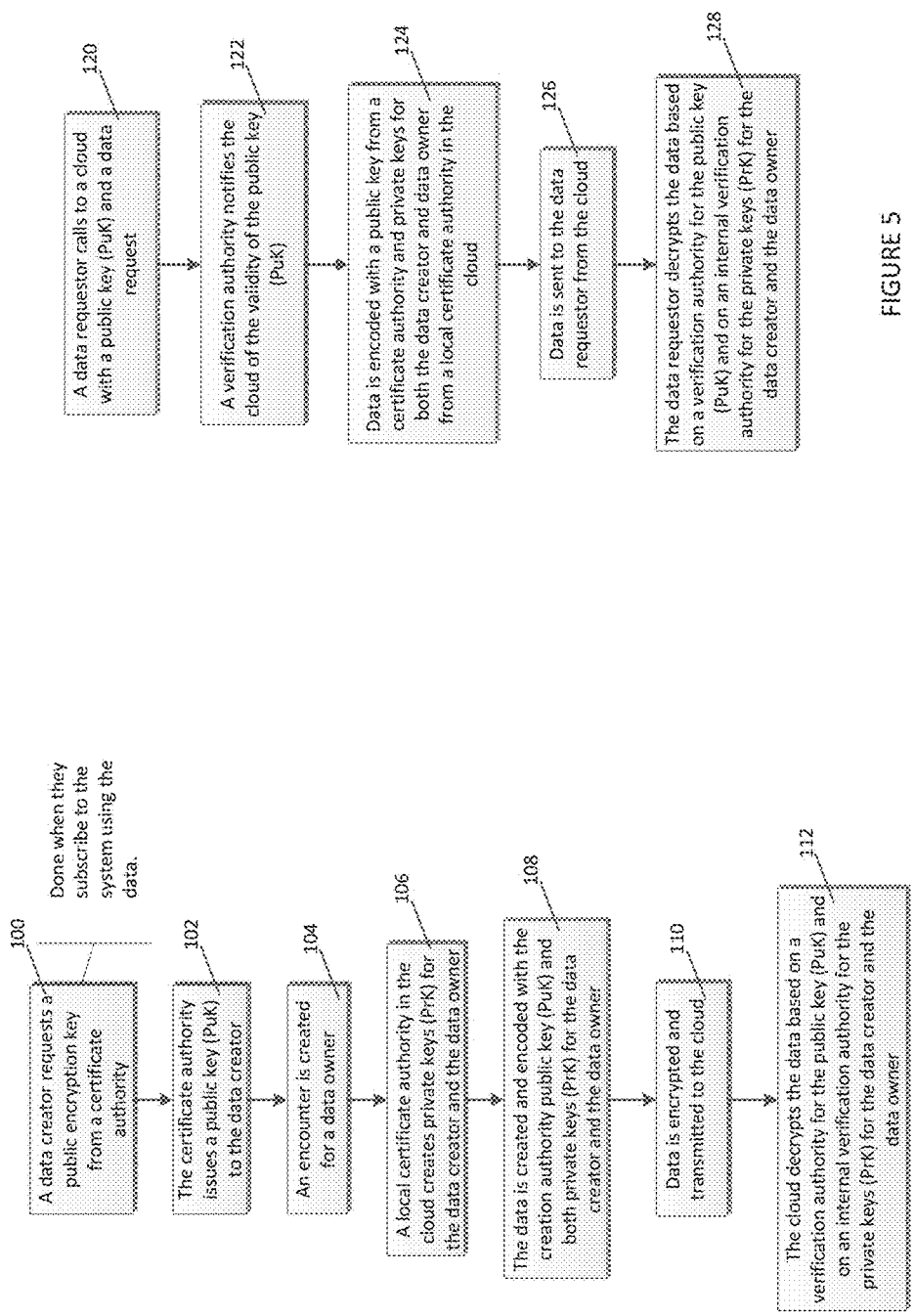

CONTROLLING ACCESS TO CLINICAL DATA ANALYZED BY REMOTE COMPUTING RESOURCES

CROSS REFERENCE TO RELATED APPLICATIONS

The present application is a continuation of U.S. application Ser. No. 14/427,324, filed Mar. 11, 2015, which is the U.S. National Phase application under 35 U.S.C. § 371 of International Application No. PCT/IB2013/058520, filed Sep. 13, 2013, which claims the benefit of U.S. Provisional Application No. 61/702,437, filed Sep. 18, 2012. These applications are hereby icorporated by reference herein.

The present application relates to analyzing clinical data by remote computing resources. It finds particular application in conjunction with systems and methods for controlling healthcare provider access to clinical data analyzed by remote computing resources and will be described with particular reference thereto. However, it is to be understood that it also finds application in other usage scenarios and is not necessarily limited to the aforementioned application.

It is essential to ensure that information being transmitted by and between the clinical resources is securely protected. Because patient medical information is confidential and protected by Federal and State laws and regulations, such as HIPAA in the US, it is important that the communicated clinical data is protected during its transmission and storage. The security of communications between clinical resources is typically enabled by controlling access to the clinical data. Specifically, the communication clinical data is encrypted to protect the content of transmitted messages so that intruders cannot read or modify the clinical data. With the growth of remote computing resources, most modern healthcare communication architectures tend to be open, interconnected environments. Sensitive clinical data no longer reside on mainframes physically isolated within a healthcare provider, where physical security measures can be taken to defend the data and the system. Clinical data is rather kept in an environment where data is outsourced to or processed on remote computing resource in order to allow de-centralized access for family doctors, medical specialists and even non-medical care providers. In order to allow sharing of clinical data among different healthcare providers or with external parties, it is advantageous to provide end-to-end security techniques such that trusted parties are allowed access to the clinical data on the network, and that the owner of the data has the ability to limit what data is accessible to others.

The present invention provides a new and improved apparatus and method which overcomes the above-referenced problems and others.

In accordance with one aspect, a method for controlling access to data being processed by a remote computing resource is provided. The method including the steps of issuing a public encryption key for a data creator from a public certificate authority, detecting an encounter with a data owner, creating private encryption keys for the data creator and the data owner in response to detecting the encounter, encrypting data being sent to the remote computing resource, decrypting the data based on public verification of the public encryption key and local verification of the data creator's private encryption key and the data owner's private encryption key at the remote computing resource, and controlling the data creator's access to the data by altering the permission of at least one of the public encryption key and data creator's private encryption key.

In accordance with another aspect, a system for controlling access to data being processed by a remote computing resource is provided. The system includes a public certificate authority which issues a public encryption key to the data creator. A data creator collects data from a data owner and encrypts the data with the public encryption key, a data creator private encryption key and a data owner encryption key. The remote computing resource decrypts the data based on public verification of the public encyrption key and local verification of the data creator's private encryption key and the data owner's private encryption key at the remote computing resource and includes a local private certification authority which creates a data creator private encryption key and a data owner encryption key in response to detecting a data owner encounter at the remote computing resource. The data owner controls the data creator's access to the data by altering the permission of at least one of the public encryption key and data creator's private encryption key.

In accordance with another aspect, a method for controlling access to data being processed by a remote computing resource is provided. The method includes issuing a public encryption key for a data creator from a public certificate authority, creating private encryption keys for the data creator and the data owner in response to detecting the encounter, encrypting data being sent to the remote computing resource with at least one of the public encryption key, the data creator's private encryption key, and the data owner's private encryption key, and decrypting and storing the data based on public verification of the public encryption key and local verification of at least one of the data creator's private encryption key and the data owner's private encryption key at the remote computing resource.

One advantage resides in providing a patient or data owner the ability to control access to clinical data being analyzed.

Another advantage resides in the ability to extend or rescind permission to access clinical data analyzed by remote computing resources.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

FIG. 3 is a block diagram of a system for verifying public and private keys issued to healthcare providers and patients in accordance with the present application.

FIG. 4 is a flowchart diagram of a method for transmitting data from a data creator to a cloud in accordance with the present application.

FIG. 5 is a flowchart diagram of a method for transmitting data from a cloud to a data creator in accordance with the present application.

Figure 1:
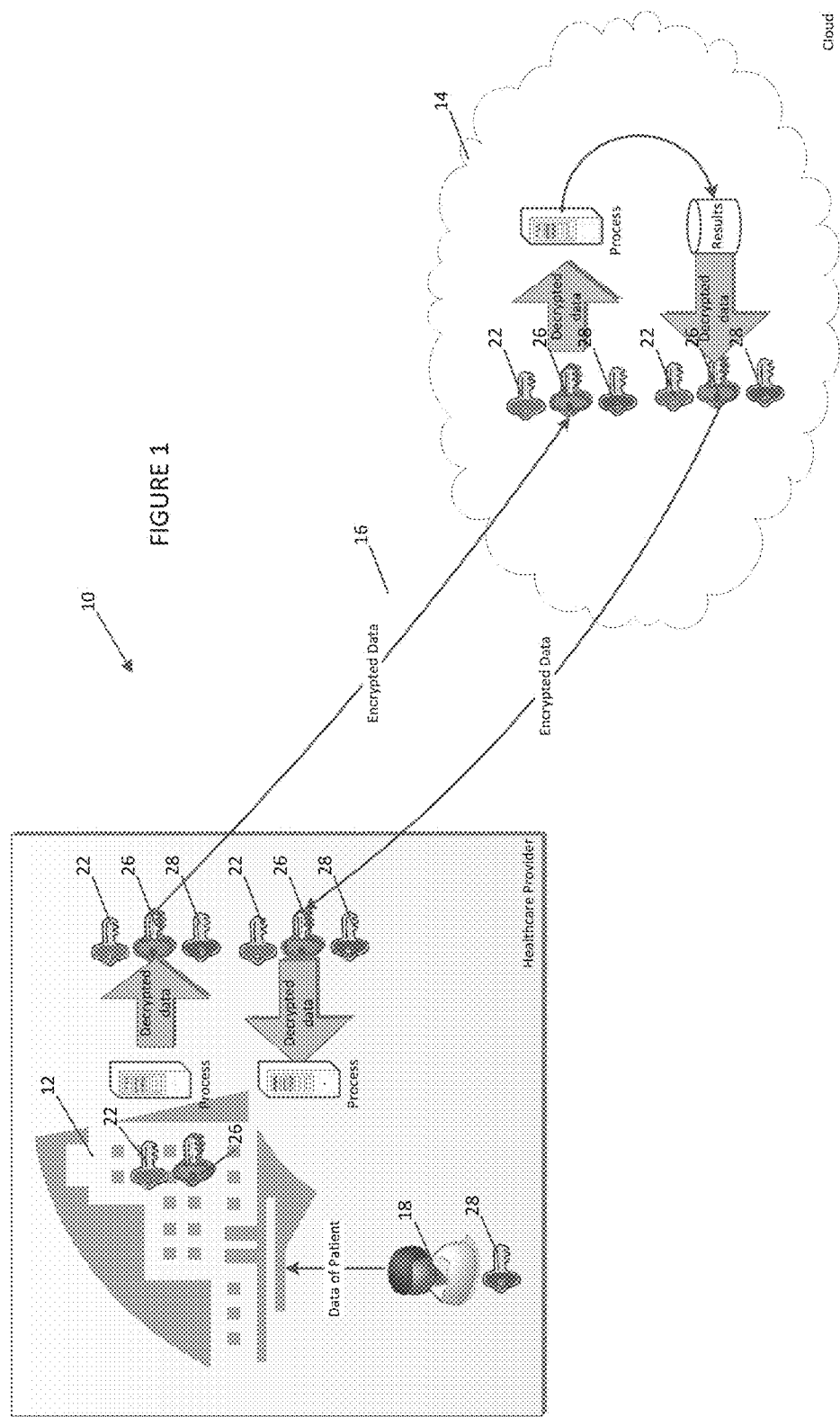
FIG. 1 is a block diagram of an IT infrastructure in accordance with the present application.

With reference to FIG. 1, a block diagram illustrates one embodiment of an information technology (IT) infrastructure 10 of a system for controlling access to clinical data analyzed by a remote computing resource. The IT infrastructure 10 suitably includes one or more healthcare systems and providers 12, a remote computing resource 14, and the like, interconnected via a communications network 16. It is contemplated that the communications network 16 includes one or more of the Intranet, a local area network, a wide area network, a wireless network, a wired network, a cellular network, a data bus, a personal area network, and the like. The healthcare provider 12 collects clinical data related to a patient 18 cared for by the healthcare system or medical institution which is analyzed by the remote computing resource 14, which in one embodiment is located in a cloud infrastructure. In other embodiments the system may be located at a single location. In yet another embodiment may exist in a secure environment, but data transmission is over public media or shared infrastructure.

As used herein, "cloud" may refer to a collection of resources (e.g., hardware, data and/or software) provided and maintained by an off-site or off-premise party (e.g., third party), wherein the collection of data and resources can be accessed by an identified user via a network. The resources can include data storage services, data processing services (e.g., applications), and many other services that are conventionally associated with and reside within personal computers, local or "on-premise" servers, having at least one processing device such as a microprocessor, graphics processor among other processing devices and associated components. In general, cloud computing may be employed to perform services in a dissociative way, i.e., the client may not know where the service is performed as long as the service is performed with the expected quality of service.

As used herein, "clinical data" may refer to data collected from a patient or from a medical institution in any number of conventional ways. For example, clinical data may be collected in the field by a healthcare provider such as a physician or clinician. Alternatively, a patient may be admitted to a healthcare provider such as a hospital or an emergency clinic and related clinical data may be collected by, for example, admissions or administration at the healthcare provider. Clinical data may be collected by other medical devices, such as, patient monitors including various subsystems for each vital sign such as SpO2, temperature, blood pressure, heart rate, etc., various imaging equipment, pacemaker monitors and interrogation devices, laboratory equipment, and other clinical data collection systems. Clinical data may also be collected by a patient's home monitoring systems, which may report physical, chemical, electrical or other patient's clinical parameters. Data collection used herein may be episodic, based on a predefined event or stochastic process, periodic, such as every 4 hours, or continuous. Data collection may be real time, near real-time or previously acquired and later uploaded.

The healthcare system, application, process, or provider (referred to as healthcare provider here forward) 12 creates data on behalf of the data owner, or processes the collected clinical data and securely transmits the clinical data to the remote computing resource 14 for analysis. After receiving the clinical data, the remote computing resource 14 processes the clinical data and generates one or more results from the analysis. For example, the remote computing resource 14 may compare the patient's clinical data with baseline clinical data, demographic data, all of which may be stored in or accessible by the remote computing resource 14. The analysis may also include the generation of one or more reports by the remote computing resource 14, which may include performance reports, clinical recommendations or advisories, or chronological graphical reports, including charts indicating healthy and unhealthy results in clear and easy to read display formats, for example. In an exemplary embodiment, result data corresponding to the results are securely transmitted back to healthcare system, provider, or actual data owner 12 for further processing.

To securely transmit the clinical and result data, the healthcare provider 12 and the remote computing resource 14 encrypt the clinical and result data to maintain the security and integrity of the data transmitted within the IT infrastructure 10. Because patient medical information is confidential and protected by Federal and State laws and regulations, such as HIPAA in the US, it is important that the communicated clinical data is protected during its transmission. The present application provides systems and methods for ensuring that all clinical data is protected while they are transmitted and that only usable by parties and processes that possess the specific set of public and private encryption keys to access such data. The transmitted data may be encrypted or scrambled, and various user access validation steps may be incorporated to protect the integrity of the data and the privacy of the patient. For example, the clinical data is encrypted before it is transmitted from the healthcare system or provider 12 to the remote computing resource 14. Once at the remote computer resource 14, the clinical data is decrypted and processed for analysis. The result data from the analysis is then encrypted again and transmitted back to the healthcare provider 12 from the remote computing resource 14 where it is decrypted for further processing.

Figure 2:
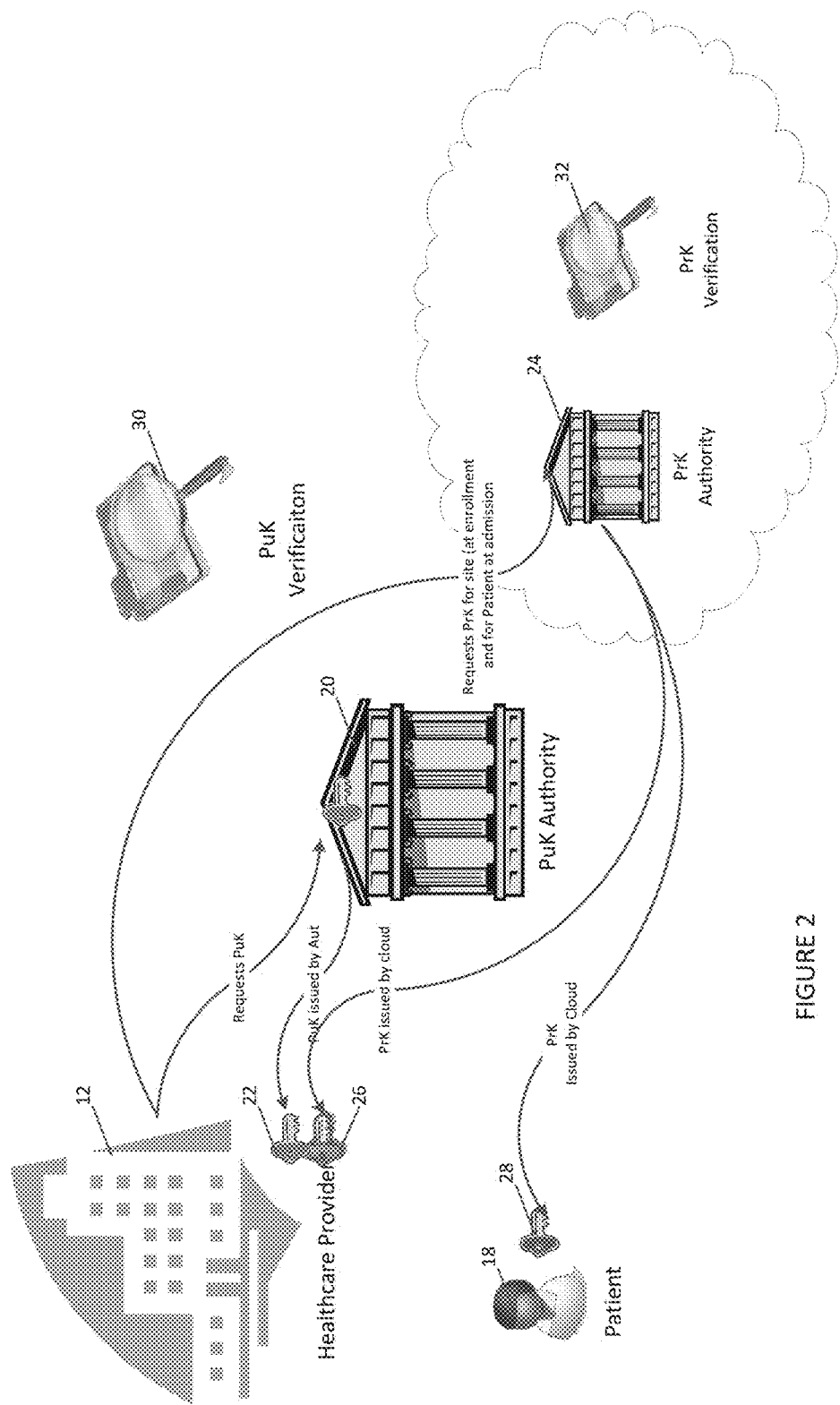
FIG. 2 is a block diagram of a system for issuing public and private keys to healthcare providers and patients in accordance with the present application.

To further maintain security and integrity of the data, public and private encryptions keys are issued to the healthcare system or provider 12 and data owner or patient (referred to as patient here forward) 18 respectively to control access to the data analyzed by remote computing resources. With reference to FIG. 2, a system for issuing public and private keys to the healthcare provider 12 and patient 18 is illustrated. When the healthcare provider 12 subscribes to the remote computer resource 14 for the processing of clinical data, the healthcare provider requests a public encryption key from a public certificate authority 20. After the health provider 12 is verified, the public certificate authority (PuK Authority) 20 issues a public encryption key 22 to the healthcare provider 12. When a patient is introduced to the healthcare provider 12, the communication of collected clinical data for processing by the remote computing resource 14 creates a patient encounter for the patient 18. In response to detecting a new patient encounter, a local private certificate authority 24 (PrK Authority) issues private encryption keys 26, 28 for healthcare provider 12 and the patient 18 respectively. In one embodiment, the private encryption keys 26, 28 for healthcare provider 12 and the patient 18 are held in escrow at the healthcare provider location until data identified for transmission for the healthcare provider and patient is identified. In another embodiment, the private encryption keys 26, 28 for healthcare provider 12 and the patient 18 are held in escrow at the remote computing resource 14.

To provide additional security and enable the user to control access, the clinical and results data are encrypted with the public encryption key 22, the healthcare provider's private encryption key 26, and the patient's private encryption key 28. For example, before the clinical data is transmitted from the healthcare provider 12 to the remote computing resource 14, the clinical data is encrypted with the public encryption key 22, the healthcare provider's private encryption key 26, and the patient's private encryption key 28. Likewise, before the results data is transmitted from the remote computing resource 14 to the healthcare provider 12, the result data is encrypted with the public encryption key 22, the healthcare provider's private encryption key 26, and the patient's private encryption key 28.

After the clinical data is encrypted and transmitted from the healthcare provider 12 to the remote computing resource 14, the remote computing resource 14 decrypts the clinical data based on a verification of the public encryption key 22, the healthcare provider's private encryption key 26, and/or the patient's private encryption key 28. Likewise, after encrypted result data is transmitted from the remote computing resource 14 to the healthcare provider 12, the healthcare provider 12 decrypts the result data based on a verification of the public encryption key 22, the healthcare provider's private encryption key 26, and/or the patient's private encryption key 28. With reference to FIG. 3, a system for verifying public and private keys of the healthcare provider 12 and patient 18 is illustrated. Specifically, the decryption of the clinical and result data is based on verification of the validity of public encryption key 22 by a public verification authority 30 (PuK Verification) located outside the cloud infrastructure and verification of the validity of the healthcare provider's private encryption key 26, and/or the patient's private encryption key 28 by a private verification authority 32 located within the cloud infrastructure. As described above, the encryption session is based on the public encryption key 22 and both the healthcare provider private encryption key 26 and the patient's private encryption key 28. The decryption session is based on the verification of the validity of the healthcare provider's public encryption key 22 and private encryption key 26 and/or the patient's private encryption key 28. Thus access to the clinical and report data is controlled by the verification of the validity of the public encryption key and the healthcare provider's private encryption key.

The additional encryption and verification protection also enables the patient to control access to the clinical data and results. Specifically, the patient 18 can authorize parties to use the existing clinical and result data by sharing the patient's private encryption key 28 with the party. Such an action does not require the healthcare provider 12 permission. In order to provide access of the clinical and results data to a party, the party would utilize its own public encryption key and the patient's private encryption key 28 to encrypt/decrypt the clinical and result data. It should also be appreciated that patient 18 can de-authorize access of the clinical and result data to the healthcare provider 12 or other parties. The patient can de-authorize application use of the existing clinical and result data, or any sub part of it by notifying the local verification authority 32 and referencing which public keys are no longer permitted to access the clinical and result data or sub part thereof.

In another embodiment, business rules based on local verification authority are established for requiring the patient's permission for which parties are permitted or rescinded from accessing particular data. For example, the local verification authority 32 includes a table of the parties that request access to the patient's data. The table enables the patient 18 to edit and match the privileges of parties to particular data sets. Further, additional business rules can be created on the patient's request to destroy aspects of the data that require the patient's permission. For example, the healthcare provider 12 will have access to data sets which they generate if the data is being utilized for performance calculations. The business rules would delete all sensitive personal information from the data and thus would not require data owner permission to access the data. Likewise, if the data does not include sensitive personal information and is suitable for secondary use (performance calculations and the like) the local verification authority requires a party to have a public encryption key to access the data.

The components of the IT infrastructure 10 suitably include processors executing computer executable instructions embodying the foregoing functionality, where the computer executable instructions are stored on memories associated with the processors. It is, however, contemplated that at least some of the foregoing functionality can be implemented in hardware without the use of processors. For example, analog circuitry can be employed. Further, the components of the IT infrastructure 10 include communication units providing the processors an interface from which to communicate over the communications network 16. Even more, although the foregoing components of the IT infrastructure 10 were discretely described, it is to be appreciated that the components can be combined.

FIG. 4 illustrates a flowchart diagram of a method for transmitting data from a data creator to a cloud. In a step 100, a data creator requests a public encryption key from a certificate authority. The request is created when the data creator subscribes to the system using the created data. In a step 102, the certificate authority issues a public key (PuK) to the data creator. In a step 104, an encounter is created for a data owner. In a step 106, a local certificate authority in the cloud creates private keys (PrK) for the data creator and the data owner. In a step 108, the data is created and encoded with the creation authority public key (PuK) and both private keys (PrK) for the data creator and the data owner. In a step 110, the data is encrypted and transmitted to the cloud. In a step 112, the cloud decrypts the data based on a verification authority for the public key (PuK) and on an internal verification authority for the private keys (PrK) for the data creator and the data owner.

FIG. 5 illustrates a flowchart diagram of a method for transmitting data from a cloud to a data creator. In a step 120, a data requestor calls to a cloud with a public key (PuK) and a data request. In a step 122, a verification authority notifies the cloud of the validity of the public key (PuK). In a step 124, the data is encoded with a public key from a certificate authority and private keys for both the data creator and data owner from a local certificate authority in the cloud. In a step 126, data is sent to the data requestor from the cloud. In a step 128, the data requestor decrypts the data based on a verification authority for the public key (PuK) and on an internal verification authority for the private keys (PrK) for the data creator and the data owner.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for controlling access to data held by a remote computing resource, the method comprising:
   receiving, from a requesting device, an identification of requested data, a public key, and a first private key;
   communicating with an external server to verify the public key;
   verifying the first private key including determining whether the requested data is locally associated with the first private key;
   transmitting the requested data to the requesting device in response to successfully verifying the public key and successfully verifying the private key;
   receiving, from an owner device, a de-authorization request including the first public key and a second private key;
   verifying the second private key including determining whether the requested data is locally associated with the second private key; and
   removing a local association between the first private key and the requested data in response to successfully verifying the second private key,
   whereby subsequent steps of verifying the first private key are unsuccessful based on the request data being locally non-associated with the first private key.

2. The method of claim 1, further comprising:
   locally generating the first public key and the second private key; and
   transmitting the first public key and the second private key to at least one of the requesting device and the owner device.

3. The method of claim 1, further comprising, prior to receiving the request for the data:
   receiving the requested data, the first private key, and the second private key;
   storing the requested data;
   locally associating the requested data with both the first private key and the second private key.

4. The method of claim 1, further comprising, prior to storing the requested data, decrypting the requested data based on the public key, the first private key, and the second private key.

5. The method of claim 1, further comprising, prior to receiving the request for the data:
   receiving clinical data, the first private key, and the second private key;
   processing the clinical data to generate the requested data;
   storing the requested data;
   locally associating the requested data with both the first private key and the second private key.

6. The method of claim 1, further comprising, prior to transmitting the requested data, encrypting the requested data based on the public key, the first private key, and the second private key.

7. A non-transitory machine-readable storage medium encoded with instructions for execution by a processor for controlling access to data held by a remote computing resource, the machine-readable storage medium comprising:
   instructions for receiving, from a requesting device, an identification of requested data, a public key, and a first private key;
   instructions for communicating with an external server to verify the public key;
   instructions for verifying the first private key including determining whether the requested data is locally associated with the first private key;
   instructions for transmitting the requested data to the requesting device in response to successfully verifying the public key and successfully verifying the private key;
   instructions for receiving, from an owner device, a de-authorization request including the first public key and a second private key;
   instructions for verifying the second private key including determining whether the requested data is locally associated with the second private key; and
   instructions for removing a local association between the first private key and the requested data in response to successfully verifying the second private key,
   whereby subsequent execution of the instructions for verifying the first private key is unsuccessful based on the request data being locally non-associated with the first private key.

8. The non-transitory machine-readable storage medium of claim 7, further comprising:
   instructions for locally generating the first public key and the second private key; and
   instructions for transmitting the first public key and the second private key to at least one of the requesting device and the owner device.

9. The non-transitory machine-readable storage medium of claim 7, further comprising instructions for, prior to receiving the request for the data:
   receiving the requested data, the first private key, and the second private key;
   storing the requested data;
   locally associating the requested data with both the first private key and the second private key.

10. The non-transitory machine-readable storage medium of claim 7, further comprising instructions for, prior to storing the requested data, decrypting the requested data based on the public key, the first private key, and the second private key.

11. The non-transitory machine-readable storage medium of claim 7, further comprising instructions for, prior to receiving the request for the data:
   receiving clinical data, the first private key, and the second private key;
   processing the clinical data to generate the requested data;
   storing the requested data;
   locally associating the requested data with both the first private key and the second private key.

12. The non-transitory machine-readable storage medium of claim 7, further comprising instructions for, prior to transmitting the requested data, encrypting the requested data based on the public key, the first private key, and the second private key.

13. A device for controlling access to data held by a remote computing resource, the device comprising:
   a storage configured to store:
      requested data;
      associations between the requested data and one or more keys;
   a communication interface; and
   a processor configured to:
      receive, from a requesting device via the communication interface, an identification of requested data, a public key, and a first private key;
      communicate via the communication interface with an external server to verify the public key;

verify the first private key including determining whether the requested data is locally associated with the first private key in the storage;

transmit, via the communication interface, the requested data to the requesting device in response to successfully verifying the public key and successfully verifying the private key;

receive, from an owner device via the communication interface, a de-authorization request including the first public key and a second private key;

verify the second private key including determining whether the requested data is locally associated with the second private key in the storage; and remove a local association between the first private key and the requested data from the storage in response to successfully verifying the second private key, whereby subsequently performing the verifying of the first private key is unsuccessful based on the request data being locally non-associated with the first private key in the storage.

14. The device of claim 13, wherein the processor is further configured to:

locally generate the first public key and the second private key; and transmit the first public key and the second private key to at least one of the requesting device and the owner device.

15. The device of claim 13, wherein the processor is further configured to, prior to receiving the request for the data:

receive the requested data, the first private key, and the second private key;

store the requested data in the storage;

locally associating the requested data with both the first private key and the second private key in the storage.

16. The device of claim 13, wherein the processor is further configured to, prior to storing the requested data, decrypt the requested data based on the public key, the first private key, and the second private key.

17. The device of claim 13, wherein the processor is further configured to, prior to receiving the request for the data:

receive clinical data, the first private key, and the second private key;

process the clinical data to generate the requested data;

storing the requested data in the storage;

locally associate the requested data with both the first private key and the second private key in the storage.

* * * * *